(12) United States Patent
Rose

(10) Patent No.: US 7,247,433 B2
(45) Date of Patent: Jul. 24, 2007

(54) TRANSCUTANEOUS IMMUNIZATION AGAINST PAPILLOMAVIRUS WITH PAPILLOMAVIRUS VIRUS-LIKE PARTICLES

(75) Inventor: Robert C. Rose, Dansville, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 10/486,564

(22) PCT Filed: Aug. 9, 2002

(86) PCT No.: PCT/US02/25391

§ 371 (c)(1),
(2), (4) Date: Aug. 24, 2004

(87) PCT Pub. No.: WO03/103570

PCT Pub. Date: Dec. 18, 2003

(65) Prior Publication Data

US 2005/0013832 A1 Jan. 20, 2005

Related U.S. Application Data

(60) Provisional application No. 60/377,023, filed on May 1, 2002, provisional application No. 60/311,901, filed on Aug. 13, 2001.

(51) Int. Cl.
*C12Q 1/68* (2006.01)
(52) U.S. Cl. ........................................ 435/6; 435/235.1
(58) Field of Classification Search .................... 435/6, 435/235.1; 424/204.1; 604/46
See application file for complete search history.

(56) References Cited

U.S. PATENT DOCUMENTS

| | | | |
|---|---|---|---|
| 5,057,411 A | 10/1991 | Lancaster et al. | |
| 5,980,898 A | 11/1999 | Glenn et al. | |
| 6,153,201 A * | 11/2000 | Rose et al. | 424/204.1 |
| 6,165,471 A | 12/2000 | Garcea et al. | |
| 6,228,368 B1 | 5/2001 | Gissmann et al. | |
| 6,595,947 B1 * | 7/2003 | Mikszta et al. | 604/27 |
| 6,835,184 B1 * | 12/2004 | Sage et al. | 604/46 |

FOREIGN PATENT DOCUMENTS

| | | |
|---|---|---|
| EP | 1 086 719 A1 | 3/2001 |
| WO | WO 93/02184 | 2/1993 |
| WO | WO 94/00152 | 1/1994 |
| WO | WO 94/05792 | 3/1994 |
| WO | WO 94/20137 | 9/1994 |
| WO | WO 96/11274 | 4/1996 |
| WO | WO 98/02548 | 1/1998 |
| WO | WO 99/43350 | 9/1999 |
| WO | WO 01/34185 A2 | 5/2001 |
| WO | WO 01/66700 A1 | 9/2001 |
| WO | WO 02/085446 A2 | 10/2002 |

OTHER PUBLICATIONS

Babiuk et al., "Cutaneous Vaccination: The Skin As An Immunologically Active Tissue and The Challenge of Antigen Delivery," *Journal of Controlled Release* 66:199-214 (2000).
Gerber et al., "Human Papillomavirus Virus-Like Particles Are Efficient Oral Immunogens when Coadministered with *Escherichia coli* Heat-Labile Enterotoxin Mutant R192G of CpG DNA," *Journal of Virology* 75(10):4752-4760 (2001).
Rose et al., "Oral Vaccination of Mice With Human Papillomavirus Virus-Like Particles Induces Systemic Virus-Neutralizing Antibodies," *Vaccine* 17:2129-2135 (1999).
Glenn et al., "Skin Immunization Made Possible by Cholera Toxin," *Nature* 391(6670):851 (1998).
Glenn et al., "Transcutaneous Immunization with Bacterial ADP-Ribosylating Exotoxins as Antigens and Adjuvants ," *Inf. Immun.* 67(3):1100-1106 (1999).
Paul et al., "Transdermal Immunization with Large Proteins by Means of Ultradeformable Drug Carriers," *Eur. J. Immunol.* 25:3521-3524 (1995).
Scharton-Kersten et al., "Principles of Transcutaneous Immunization Using Cholera Toxin As an Adjuvant," *Vaccine* 17(Supp. 2):S37-S43 (1999).
Howley, P.M., "The Viruses and Their Replication," in 2 Virology 2045-2076, 2047 (Bernard N. Fields et al. eds., 3d ed. 1995).

* cited by examiner

*Primary Examiner*—Ali R. Salimi
(74) *Attorney, Agent, or Firm*—Nixon Peabody LLP

(57) ABSTRACT

The present invention relates to a method of vaccinating a mammal against papillomavirus by administering papillomavirus virus-like particles transdermally to a mammal under conditions effective to induce an immune response to the papillomavirus.

13 Claims, 5 Drawing Sheets

TRANSCUTANEOUS IMMUNIZATION AGAINST PAPILLOMAVIRUS WITH PAPILLOMAVIRUS VIRUS-LIKE PARTICLES

This application is a 371 of PCT/US02/25391 which claims benefit of U.S. Provisional Patent Application Ser. Nos. 60/377,023, filed May 1, 2002, and 60/311,801, filed Aug. 13, 2001.

The United States Government may have certain rights in this invention pursuant to a Public Health Service award from the National Institutes of Health (Grant No. 1RO1 CA 84105-01).

FIELD OF THE INVENTION

The present invention relates to the transcutaneous immunization against papillomaviruses with papillomavirus virus-like particles.

BACKGROUND OF THE INVENTION

The family Papovaviridae constitutes a group of DNA viruses that induce both lytic infections and either benign or malignant tumors. Structurally, all are naked icosahedral virions with 72 capsomeres and contain double-stranded circular DNA. Viruses included in the family are: (1) human and animal papillomaviruses, (2) mouse polyomavirus, (3) simian vacuolating virus, and (4) human viruses BK and JC.

Human papillomaviruses (HPV) infect cutaneous, genital, oral, and respiratory epithelia in a tissue-specific manner. Infection with HPV has been associated closely with the development of both benign lesions and malignancies (Reichman et al., *Papilomaviruses*, pp. 1191–1200 (1990); and Mandell et al., *Principles and Practice of Infectious Diseases*, 3rd Edition, Churchill Livingstone, New York, N.Y.). For example, HPV type 1 (HPV-1) is present in plantar warts, HPV types 6 or 11 (HPV-6 or HPV-11) in condylomata acuminata (anogenital warts), while HPV types 16 or 18 (HPV-16 or HPV-18) are common in premalignant and malignant lesions of the cervical squamous epithelium (See Crum et al., "Human Papillomavirus Infection and Cervical Neoplasia: New Perspectives," *Int. J. Gynecol. Pathol.* 3:376–388 (1984); zur Hausen, *Genital Papillomavirus Infections*, pp. 83–90 (1985); Rigby et al., *Viruses and Cancer*, Cambridge University Press, Cambridge, UK; and Koutsky et al., "Epidermology of Genital Human Papillomavirus Infection," *Epidemiol. Rev.* 10:122–163 (1988)).

However, difficulties in propagating HPV in vitro has led to the development of alternative approaches to antigen production for immunologic studies. For example, Bonnez et al., "The PstI-XhoII Restriction Fragment of the HPV-6b L1 ORF Lacks Immunological Specificity as Determined by Sera from HPV 6 Condyloma Acuminatum Patients and Controls," *UCLA Symp. Mol. Cell. Biol.*, New Series, 124: 77–80 (1990); Jenison et al., "Identification of Immunoreactive Antigens of Human Papillomavirus Type 6b by Using *Escherichia coli*-Expressed Fusion Proteins," *J. Virol.* 62:2115–2123 (1988); Li et al., "Identification of the Human Papillomavirus Type 6b L1 Open Reading Frame Protein in Condylomas and Corresponding Antibodies in Human Sera," *J. Virol.* 61:2684–2690 (1987); Steele et al., "Humoral Assays of Human Sera to Disrupted and Nondisrupted Epitopes of Human Papillomavirus Type 1," *Virology* 174:388–398 (1990); and Strike et al., "Expression in *Escherichia coli* of Seven DNA Segments Comprising the Complete L1 and L2 Open Reading Frames of Human Papillomavirus Type 6b and the Location of the 'Common Antigen'," *J. Gen. Virol.* 70:543–555 (1989), have expressed recombinant capsid protein coding sequences in prokaryotic systems, and used them in Western blot analyses of sera obtained from individuals with HPV infection of the genital tract. Results from these studies have suggested that antibodies to denatured, i.e. linear, epitopes of HPV capsid proteins can be detected in the sera of some infected individuals.

Whole virus particles have also been used to detect antibodies in human sera, including antibodies directed against conformational epitopes. These studies have been difficult to conduct, because most naturally occurring HPV-induced lesions produce few particles. Whole virus particles can be obtained, however, in amounts sufficient to conduct immunologic assays from HPV type 1-induced plantar warts (Kienzler et al., "Humoral and Cell-Mediated Immunity to Human Papillomavirus Type 1 (HPV-1) in Human Warts," *Br. J. Dermatol.* 108:65–672 (1983); "Pfister et al., Seroepidemiological Studies of Human Papilloma Virus (HPV-1) Infections," *Int. J. Cancer* 21:161–165 (1978); and Steele et al., "Humoral Assays of Human Sera to Disrupted and Nondisrupted Epitopes of Human Papillomavirus Type 1," *Virology* 174:388–398 (1992)) and experimentally-induced HPV-11 athymic mouse xenographs (Kreider et al., "Laboratory Production in vivo of Infectious Human Papillomavirus Type 11," *J. Virol.* 61:590–593 (1991); and Kreider et al., "Morphological Transformation in vivo of Human Uterine Cervix With Papillomavirus from Condylomata Acuminata," *Nature* 317:639–641 (1985)). More particularly, U.S. Pat. No. 5,071,757 to Kreider et al., discloses a method of propagating infectious HPV-11 virions in the laboratory using an athymic mouse xenograph model system. Although this system is capable of producing quantities of infectious virus that could be used for the development of a serologic test for genital HPV infection, this system is very expensive and cumbersome. Furthermore, only one genital HPV type has so far been propagated in this system, thus, limiting its usefulness. In addition, the infectious virus produced using this system represents a biohazard and, therefore, would be difficult to use in a vaccine formulation Zhou et al., in "Expression of Vaccinia Recombinant HPV 16 L1 and L2 ORF Proteins in Epithelial Cells is Sufficient for Assembly of HPV Virion-like Particles", *Virology* 185:251–257 (1992), have reported the formation of HPV-16 virus-like particles in CV-1 cell nuclei following infection with a vaccinia virus HPV-16 L1/L2 double recombinant expression vector. However, the authors were not able to produce VLPs with a vector expressing L1 alone. Furthermore, the VLPs produced lacked a well-defined symmetry, and were more variable in size and smaller, only about 35–40 nm in diameter, than either HPV virions (55 nm) or the VLPs of the present invention (baculovirus produced HPV-11 VLPs, about 50 nm in diameter).

U.S. Pat. No. 5,045,447, to Minson, discloses a method of screening hybridoma culture supernatants for monoclonal antibodies with desired specificities. Minson's method is exemplified by the production of antibodies to the L1 protein of human papillomavirus type 16 (HPV-16) using this protein as the target antigen in mice. However, Minson fails to disclose the expression of the L1 protein or production of HPV virus-like particles (VLPs).

U.S. Pat. No. 4,777,239, to Schoolnik et al., discloses short peptide sequences derived from several of the papillomavirus early region open reading frames which elicit type-specific antibodies to papillomavirus. However, the inventors fail to disclose any sequences directed to the major late open reading frame, L1.

U.S. Pat. No. 5,057,411 to Lancaster et al., discloses a polynucleotide sequence of about 30 nucleotides of the papillomavirus L1 capsid protein open reading frame that the inventors contend encode a papillomavirus type-specific epitope. However, the inventors do not disclose infected animals that produced antibodies which recognize this sequence. Instead, they synthesized a bovine papillomavirus type 1 (BPV-1) version of the sequence (a 10 amino acid peptide, or decapeptide), then immunized rabbits and tested the antiserum's ability to react with either BPV-1 or BPV-2 induced fibropapilloma tissue. The peptide antiserum only reacted with BPV-1 and not BPV-2 tissue. The inventors then concluded that the peptide contained an antigenic determinant that was type-specific, and therefore, all papillomavirus L1 coding sequences contain a type-specific epitope at this locus. This is theoretical speculation on the part of the inventors, who give no supporting data for this hypothesis. In addition, the amino acid sequences disclosed (i.e. 10 amino acids) are generally thought not to be capable of adopting higher order antigenic structures, i.e., conformational epitopes that possess a three-dimensional structure such as those produced by the method described herein.

Another problem associated with papillomavirus infections is the need for alternative therapeutic and prophylactic modalities. In 1944, Biberstein treated condyloma acuminatum patients with an autogenous vaccine derived from the patients' warts (Biberstein, "Immunization Therapy of Warts," *Arch. Dermatol Syphilol.* 50:12–22 (1944)). Thereafter, Powell et al., developed the technique typically used today for preparing autogenous wart vaccines for the treatment of condyloma acuminatum (Powell et al., "Treatment of Condylomata Acuminata by Autogenous Vaccine," *South Med. J.* 63:202–205 (1970)). Only one double-blind, placebo-controlled study has attempted to evaluate the efficacy of the autogenous vaccine (Malison et al., "Autogenous Vaccine Therapy for Condyloma Acuminatum A Double-blind Controlled Study," *Br. J. Vener. Dis.* 58:62–65 (1982)). The authors concluded that autogenous vaccination was not effective in the treatment of condylomata acuminata, although this interpretation may be erroneous. The small number of patients studied precluded drawing valid negative conclusions. ID any event, autogenous vaccines, as presently described, have several disadvantages. First, the patient needs to have relatively large warts (2 g to 5 g) in order to prepare the vaccine. Secondly, the practitioner needs access to laboratory equipment and expertise each time a new patient is to be treated. Thus, vaccine preparation is very expensive, tedious, and in cases involving relatively small lesion mass, not possible.

The present invention is directed to overcoming these deficiencies in the art.

SUMMARY OF THE INVENTION

The present invention relates to a method of vaccinating a mammal against papillomavirus by administering papillomavirus virus-like particles transcutaneously to the mammal under conditions effective to induce an immune response to the papillomavirus.

Immunization, in accordance with the present invention, could be given by untrained personnel, and is amenable to self-application. Large-scale field immunization could occur given the easy accessibility to immunization. Additionally, a simple immunization procedure would improve access to immunization by pediatric patients and the elderly, and populations in Third World countries.

For previous vaccines, their formulations were injected through the skin with needles. Injection of vaccines using needles carries certain drawbacks including the need for sterile needles and syringes, trained medical personnel to administer the vaccine, discomfort from the injection, and potential complications brought about by puncturing the skin with the needle. Immunization through the skin without the use of needles (i.e. transcutaneous immunization) represents a major advance for vaccine delivery by avoiding the aforementioned drawbacks.

The transcutaneous delivery system of the invention is also not concerned with penetration of intact skin by sound or electrical energy. Such a system that uses an electrical field to induce dielectric breakdown of the stratum corneum is disclosed in U.S. Pat. No. 5,464,386 to Hofmann, which is hereby incorporated by reference in its entirety.

Moreover, transcutaneous immunizations may be superior to immunization using needles as more immune cells would be targeted by the use of several locations targeting large surface areas of skin. A therapeutically effective amount of antigen sufficient to induce an immune response may be delivered transcutaneously either at a single cutaneous location, or over an area of intact skin covering multiple draining lymph node fields (e.g., cervical, axillary, inguinal, epitrochlear, popliteal, those of the abdomen and thorax). Such locations close to numerous different lymphatic nodes at locations all over the body will provide a more widespread stimulus to the immune system than when a small amount of antigen is injected at a single location by intradermal subcutaneous or intramuscular injection.

Antigen passing through or into the skin may encounter antigen presenting cells which process the antigen in a way that induces an immune response. Multiple immunization sites may recruit a greater number of antigen presenting cells and the larger populations of antigen presenting cells that were recruited would result in greater induction of the immune response. It is conceivable that absorption through the skin may deliver antigen to phagocytic cells of the skin such as, dermal dendritic cells, macrophages, and other skin antigen presenting cells; antigen may also be delivered to phagocytic cells of the liver, spleen, and bone marrow that are known to serve as the antigen presenting cells through the blood stream or lymphatic system The result would be widespread distribution of antigen to antigen presenting cells to a degree that is rarely, if ever achieved, by current immunization practices.

Transcutaneous immunization offers certain advantages over other routes of vaccination. For example, transcutaneous vaccines are more easily administered and, thus, may be more acceptable to vaccine recipients. Also, transcutaneous vaccines can be less pure than vaccines formulated for injection, making production costs lower. Interestingly, in some instances transcutaneously administered antigens have been shown to elicit mucosal immune responses, which may be important for protection against infection with certain pathogens (Glenn, et al., "Transcutaneous Immunization with Cholera-toxin Protects Mice Against Lethal Mucosal Toxin Challenge," *J. Immunol.* 161(7):3221–4 (1998) and Gockel, et al., "Transcutaneous Immunization Induced Mucosal and Systemic Immunity: A Potent Method for Targeting Immunity to the Female Reproductive Tract," *Molec. Immun.* 37(9):537–44 (2000)), which are hereby incorporated by reference in their entirety).

Roughly 450,000 new cases of invasive uterine cervical carcinoma are diagnosed annually worldwide (Munos, N., "Disease-Burden Related to Cancer Induced by Viruses and H. pylori," *World Health Organization (WHO) Vaccine*

Research and Development: Report of the Technical Review Group Meeting (1997), which is hereby incorporated by reference in its entirety). Therefore, efficient methods of vaccine delivery will be needed for the immunization of large numbers of susceptible individuals. Thus, transcutaneous immunization strategies will certainly facilitate implementation of mass immunization programs designed to reduce the incidence of cervical cancer and other HPV-associated diseases.

Long-term low-level immune stimulation via a convenient needle-free transdermal immunization method may be particularly useful for priming naïve individuals for subsequent booster immunizations and, thus, can potentially reduce the number of booster immunizations required and the amount of antigen required to achieve an immune response adequate for protection from disease. As a result, transdermal immunization may be useful for reducing the cost of immunization

DETAILED DESCRIPTION OF THE INVENTION

Figure 1:
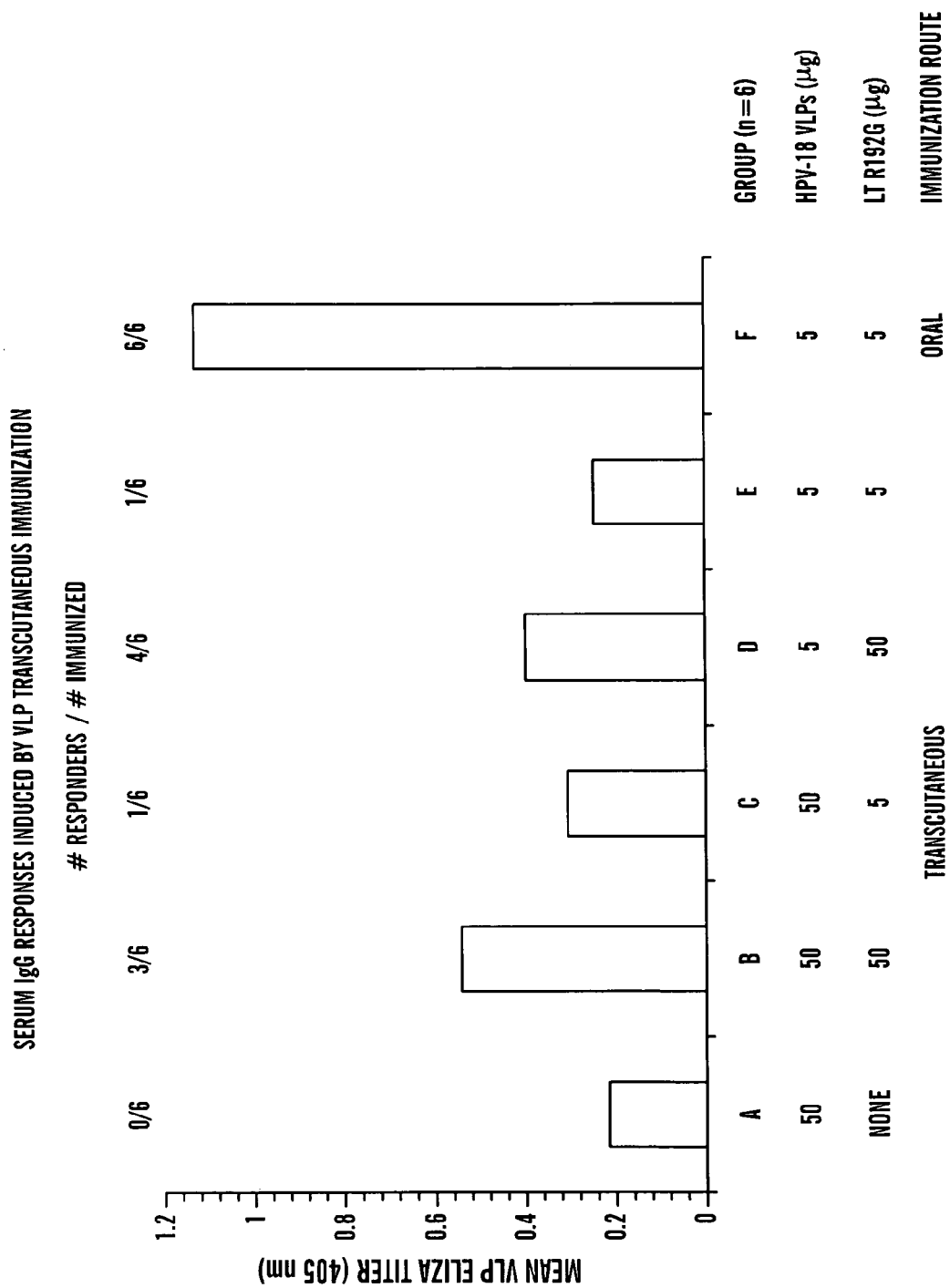
FIG. 1 shows the serum IgG responses after transcutaneous immunization with HPV-18 VLPs. Female BALB/c mice (6/group) were immunized as indicated, sera were collected and evaluated by ELISA against HPV-18 VLPs as previously described (Rose et al., "Serological Differentiation of Human Papillomavirus Types 11, 16 and 18 Using Recombinant Virus-like Particles," *Journal of General Virology* 75:2445–2449 (1994); Rose et al., "Human Papillomavirus Type 11 Recombinant L1 Capsomeres Induce Virus-Neutralizing Antibodies," *Journal of Virology* 72(7): 6151–6154 (1998); Rose et al., "Oral Vaccination of Mice with Human Papillomavirus Virus-like Particles Induces Systemic Virus-Neutralizing Antibodies," *Vaccine* 17:2129–2135 (1999), which are hereby incorporated by reference in their entirety).

The present invention relates to a method of vaccinating a mammal against papillomavirus by administering papillomavirus virus-like particles transcutaneously to the mammal under conditions effective to induce an immune response to the papillomavirus.

As used herein, "virus-like particle(s) (VLPs)" refer to a virus-like particle(s), fragment(s), capsomer(s) or portion(s) thereof produced from the capsid protein coding sequence of papillomavirus and comprising antigenic characteristic(s) similar to those of infectious papillomavirus particles. As used herein, "antigenic characteristic(s)" refers to (1) the ability of the virus-like particle(s) to cross-react with wild-type particles (native infectious virus particles of the same HPV type) as determined by antisera generated in animals and/or humans by immunization with either VLPs or infectious virus; and/or (2) the ability to recognize or detect antibodies in human sera from persons known to be infected with homologous virus.

As used herein, "L1 protein coding sequence" or "L1 capsid protein coding sequence" or "L1 coding sequence" refers to the open reading frame which codes for the L1 protein in papillomavirus. When expressed, the L1 protein coding sequence produces a protein, or protein complex, or aggregate, which possesses immunological and morphological characteristics similar to those of native papillomavirus virions. The L1 coding sequence used in the invention can be isolated and purified from papillomavirus genomic DNA or synthesized using standard genetic engineering techniques.

As used herein, the term "transfecting" refers to any means for introducing a virus, plasmid or vector into a cell. Examples of such means include infection, calcium phosphate precipitation and electroporation.

In accordance with the present invention, there is provided a method of expressing the coding sequence for the L1 capsid protein of human papillomavirus type-11 (HPV-11) or human papillomavirus type-6 (HPV-6) in Sf-9 insect cells using the baculovirus expression system. The HPV-6 and HPV-11 coding sequences were cloned using standard techniques in the art into a baculovirus transfer vector. The resulting baculovirus transfer vector were used to co-transfect Sf-9 insect cells with *Autographa californica* nuclear polyhedrosis virus (AcNPV) forming a recombinant baculovirus (Ac6L1 or Ac11L1) which was recovered. Sf-9 insect cells were thereafter infected with either Ac6L1 or Ac11L1 under conditions facilitating expression of the protein in the cells. It was discovered that the L1 protein formed virus-like particles (VLPs). VLPs were identified by electron microscopy of negatively-stained sucrose band fractions obtained from Sf-9 cells infected with the Ac11L1 recombinant baculovirus. It was further discovered that the VLPs possessed immunological and morphological characteristics similar to those of native HPV-11 virions, as defined by rabbit antisera. It is understood that the capsid protein coding sequences of these HPV types are used for purposes of illustration only, and that any L1 capsid protein coding sequence for any animal or human papillomavirus type can be used without deviating from the intended scope of the invention.

Many HPV L1 DNAs have been reported in the literature and are publicly available. (See, e.g., Baker, "Sequence Analysis of Papillomavirus", *Genomes*, pp.321–384; U.S. Pat. No. 5,437,931 to Long et al., Cole et al., *J. Mol. Biol.*, 193:599–608 (1987); Danos et al., *EMBO J.*, 1:231–236 (1982); Cole et al., *J. Virol.*, 38(3)991–995 (1986).) Also, it is well known that HPV L1 DNAs exhibit significant homology. Therefore, a desired HPV L1 DNA can easily be obtained, e.g., by the use of a previously reported HPV L1 DNA or a fragment thereof as a hybridization probe or as a primer during polymerization chain reaction (PCR) amplification. Indeed, numerous HPV L1 DNAs have been cloned and expressed.

Preferably, the HPV L1 DNA of the present invention will be derived from an HPV which is involved in cancer or condyloma acuminata, e.g., HPV-16, HPV-18, HPV-31, HPV-33, HPV-35, HPV-39, HPV-45, HPV-51, HPV-52, and HPV-56, which are involved in cancer, and HPV-6, HPV-11, HPV-30, HPV-42, HPV-43, HPV-44, HPV-54, HPV-55, and HPV-70, which are involved in warts. However, the subject virus-like particles may be produced from any desired HPV L1 DNA.

The preferred expression system used is the baculovirus expression system, however, it is understood that any other expression system(s) can be employed herein provided the system(s) can express the L1 protein coding sequence. Examples of such systems include, without limitation, any prokaryotic and/or eukaryotic system(s) including adenovirus, SV40, *E. coli*, CHO cells, vaccinia virus, insect viruses, yeast, bacteriophage virus or modified viruses, DNA plasmids, vectors and the like.

The host cell for expression of the L1 coding sequence is dependent on the expression system used. Examples of suitable host cells include, without limitation, bacteria (prokaryotic), microorganisms such as yeast, mammalian cells (eukaryotic) and insect cells. When using the baculovirus expression system, insect cells, such as Sf-9 or Sf-21 are preferred.

Suitable procedures for producing capsomeres are set forth in U.S. Pat. No. 6,165,471 to Garcea, et al., which is hereby incorporated by reference in its entirety.

It was discovered that the L1 protein produces virus-like particles (VLPs), fragment(s), capsomer(s) or portion(s) thereof, formed from papillomavirus capsid protein. It has been discovered that the virus-like particle(s) comprises antigenic characteristic(s) similar to those of native infectious papillomavirus particles. More particularly, these VLPs contain an antigenic determinant that is specifically recognized by antibodies present in sera obtained from genital HPV-infected patients. For example, reaction of VLP-containing insect cell extracts with antisera directed against either denatured or non-denatured capsid epitopes, as deduced by immunoreactivities in Western blot and immunodotblot assays, suggested that conformational epitopes present in native HPV-11 infectious virions were also present on the baculovirus-produced HPV-11 VLPs of the present invention. Immunodotblot assays using human sera obtained from individuals with biopsy proven condylomata acuminatum correlated closely with results previously obtained in HPV-11 whole virus particle-based ELISA tests as described by Bonnez et al., "Use of Human Papillomavirus Type 11 Virions in an ELISA to Detect Specific Antibodies in Humans with Condylomata Acuminata," *J. Gen. Virol.* 72:1343–1347 (1991), which is hereby incorporated by reference in its entirety.

These morphologic and immunologic similarities to native HPV-11 virions suggest that recombinant VLPs produced in the baculovirus system will be useful in sero-epidemiology and pathogenesis studies of not only genital HPV infection but for any papillomavirus and for vaccine development. L1 has an intrinsic capacity for self-assembly. Thus, other papillomavirus proteins are not required for VLP formation in the baculovirus system This supports the contention that VLPs to all types of papillomaviruses can be produced in accordance with the method described herein.

The VLPs of the present invention can be used to raise antibodies, either in subjects for which protection against infection by HPV is desired, i.e., vaccines, or to heighten the immune response to an HPV infection already present. In addition to polyclonal antisera, monoclonal antibodies can be obtained using the methods of Kohler and Milstein, or by modifications thereof, by immortalizing spleen or other antibody-producing cells from injected animals to obtain antibody-producing clones, i.e., hybridomas.

The antibodies obtained can be used for passive therapy, taking into account species variations.

The VLPs of the invention can be directly administered to a host to induce the formation of neutralizing antibodies (Bonnez et al., "Antibody-Mediated Neutralization of Human Papillomavirus Type 11 (HPV-11) Infection in the Nude Mouse: Detection of HPV-11 mRNAs by the Polymerase Chain Reaction," *J. Inf. Dis.* 165: 376–380 (1992); Rose, R. C., et al., "Human Papillomavirus (HPV) Type 11 Recombinant Virus-Like Particles Induce the Formation of Neutralizing Antibodies and Detect HPV-Specific Antibodies in Human Sera," *J. Gen. Virol.* 75:2075–2079 (1994), which are hereby incorporated by reference in their entirety), to confer either protective immunity against HPV or, if the patient is already infected, to boost the patient's own immune response. For all applications, the VLPs are administered in immunogenic form Optionally, the VLPs can be conjugated to an immunogenicity conferring carrier material, the material preferably being antigenically neutral. Depending on the use required, the VLPs of the invention have the ability to serve as type specific or broad range vaccines and diagnostics.

VLPs which are to be administered as vaccines can be formulated according to conventional and/or future methods for such administration to the subject to be protected and can be mixed with conventional adjuvants. The peptide expressed can be used as an immunogen in subunit vaccine formulations, which may be multivalent. The multivalent vaccine formulation can comprise VLPs each encoding a different L1 protein from different HPVs. The product may be purified for purposes of vaccine formulation from any vector/host systems that express the heterologous protein. The purified VLPs should be adjusted to an appropriate concentration, formulated with any suitable vaccine adjuvant and packaged for use. Suitable adjuvants include, but are not limited to: mineral gels, e.g., aluminum hydroxide; surface active substances such as lysolecithin, pluronic polyols; polyanions; peptides; oil emulsions; and potentially useful human adjuvants such as BCG (Bacille Calmette-Guerin) and *Corynebacterium parvum*. The immunogen may also be incorporated into liposomes, or conjugated to polysaccharides and/or other polymers for use in a vaccine formulation If they are to be used to produce antibodies for diagnostic purposes, convenient test animals can be used to prepare the appropriate antis era Suitable hosts include mice, rats, rabbits, guinea pigs, or even larger mammals such as sheep. The antibodies can be used therapeutically so long as they are compatible with the host to be treated. Monoclonal antibodies having the proper species characteristics are preferred for this application.

The present invention provides a method of vaccinating a mammal against papillomavirus by administering papillomavirus virus-like particles transcutaneously to a mammal under conditions effective to induce an immune response to the papillomavirus.

Transcutaneous immunization requires both passage of an antigen through the outer barriers of the skin which were normally imperious to such passage and an immune response to the antigen. In order to obtain a high degree of protection, the method may also involve administering one or more vaccine booster inoculations of papillomavirus virus-like particles parenterally, transcutaneously, or orally to the mammal. In a preferred embodiment of the invention, the immune response induced by transcutaneous immunization will protect the mammal from infection by a papillomavirus.

The preferred papillomavirus is a human papillomavirus, in particular Human Papillomavirus Type 6 and Type 11.

The present invention also provides transcutaneous vaccines having papillomavirus virus-like particles and a pharmaceutically acceptable carrier. In addition, transcutaneous vaccines may also contain stabilizers and preservatives to extend the shelf life of the vaccine.

Prophylactic vaccination with recombinant VLPs has emerged as a strategy for the prevention of anogenital HPV infection (Kirnbauer, R., "Papillomavirus-Like Particles For Serology and Vaccine Development," *Intervirology* 39(1–2): 54–61 (1996); Rose, R. C., et al., "Human Papillomavirus Infections," p. 343–368. In G. J. Galasso, R. J. Whitley, and T. C. Merigan (eds.), "Antiviral Agents and Human Viral Diseases," 4*th* ed. Lippincott-Raven Publishers, Philadelphia (1997); Schiller, J. T., et al., "Papillomavirus-Like Particles and HPV Vaccine Development," *Seminars in Cancer Biology* 7(6):373–382 (1996), which are hereby incorporated by reference in their entirety). VLPs are highly immunogenic when administered parenterally (Kirnbauer, R. F., et al., "Papillomavirus L1 Major Capsid Protein Self-Assembles into Virus-Like Particles That Are Highly Immunogenic," *Proceedings of the National Academy of Sciences of the United States of America* 89(24):12180–12184 (1992); Rose, R. C., et al., "Human Papillomavirus (HPV) Type 11 Recombinant Virus-Like Particles Induce the Formation of Neutralzing Antibodies and Detect HPV-Specific Antibodies in Human Sera," *J. Gen. Virol.* 75:2075–2079 (1994), which are hereby incorporated by reference in their entirety), and have been shown to elicit protective immune responses (Breitburd, F., et al., "Immunization With Virus-Like Particles From Cottontail Rabbit Papillomavirus (CRPV) Can Protect Against Experimental CRPV Infection," *J. Virology* 69(6):3959–3963 (1995); Christensen, N. D., et al., "Assembled Baculovirus-Expressed Human Papillomavirus Type 11 L1 Capsid Protein Virus-Like Particles Are Recognized By Neutralizing Monoclonal Antibodies and Induce High Titres of Neutralizing Antibodies," *J. Gen. Virol.* 75:2271–2276 (1994); Kirnbauer, R., et al., "Virus-Like Particles of Bovine Papillomavirus Type 4 in Prophylactic and Therapeutic Immunization," *Virology* 219(1):37–44 (1996); Rose, R. C., et al., "Human Papillomavirus (HPV) Type 11 Recombinant Virus-Like Particles Induce the Formation of Neutralizing Antibodies and Detect HPV-Specific Antibodies in Human Sera," *J. Gen. Virol.* 75:2075–2079 (1994); Suzich, J. A., et al., "Systemic Immunization With Papillomavirus L1 Protein Completely Prevents the Development of Viral Mucosal Papillomas," *Proc. Natl. Acad. Sci.*, USA 92:11553–11557 (1995); White, W. I., et al., "In Vitro Infection and Type-Restricted Antibody-Mediated Neutralization of Authentic Human Papillomavirus Type 16," *J. Virology* 72:959–964 (1998), which are hereby incorporated by reference by their entirety). The present results demonstrate that similar responses can be induced by transcutaneous VLP immunization. Antigenic specificities of transcutaneously induced antibodies were found to be dependent on native VLP structure, and restricted according to HPV genotype. The detection of antigen structure-dependent antibody specificity in the murine post-immune sera indicated that HPV-18 VLPs maintained their native structure and antigenicity. This demonstrates the usefulness of VLPs as transcutaneous immunogens for the prevention of anogenital HPV disease.

An object of the present invention is to provide a novel means for immunization through intact skin without the need for perforating the skin. The transcutaneous immunization system provides a method whereby antigens and adjuvants can be delivered to the immune system, especially specialized antigen presentation cells underlying the skin, such as Langerhans cells.

Without being bound to any particular theory, it is presumed that the transcutaneous immunization delivery system carries antigen to cells of the immune system where an immune response is induced The antigen may pass through the normal protective outer layers of the skin (i.e., stratum corneum) and induce the immune response directly, or through an antigen presenting cell (e.g., macrophage, tissue macrophage, Langerhans cell, dendritic cell, dermal dendritic cell, B lymphocyte, or Kuppfer cell) that presents processed antigen to a T lymphocyte.

Optionally, the antigen may pass through the stratum corneum via a hair follicle or a skin organelle (e.g., sweat gland, oil gland).

Transcutaneous immunization with HPV virus-like particles may target the epidermal Langerhans cell, known to be among the most efficient of the antigen presenting cells (APCs). bAREs activate Langerhans cells when applied epicutaneously to the skin in saline solution. The Langerhans cells direct specific immune responses through phagocytosis of the antigens, and migration to the lymph nodes where they act as APCs to present the antigen to lymphocytes, and thereby induce a potent antibody response. Although the skin is generally considered a barrier to invading organisms, the imperfection of this barrier is attested to by the numerous Langerhans cells distributed throughout the epidermis that are designed to orchestrate the immune response against organisms invading via the skin.

According to U.S. Pat. No. 5,980,898 to Glenn, et. al., which is hereby incorporated by reference in its entirety, the potent antigen presenting capability of the epidermal Langerhans cells can be exploited for transcutaneouly delivered vaccines. A transcutaneous immune response using the skin immune system would require delivery of vaccine antigen only to Langerhans cells in the stratum corneum (the outermost layer of the skin consisting of cornified cells and lipids) via passive diffusion and subsequent activation of the Langerhans cells to take up antigen, migrate to B-cell follicles and/or T-cell dependent regions, and present the antigen to B and/or T cells. If antigens other than bARES (e.g., BSA) were to be phagocytosed by the Langerhans cells, then these antigens could also be taken to the lymph node for presentation to T-cells and subsequently induce an immune response specific for that antigen (e.g., BSA). Thus, a feature of transcutaneous immunization is the activation of the Langerhans cell, presumably by a bacterial ADP-ribosylating exotoxin, ADP-ribosylating exotoxin binding subunits (e.g., cholera toxin B subunit), or other Langerhans cell activating substance.

The mechanism of transcutaneous immunization via Langerhans cells activation, migration, and antigen presentation is clearly shown by the upregulation of MHC class II expression in the epidermal Langerhans cells from epidermal sheets transcutaneously immunized with CT or CTB. In addition, the magnitude of the antibody response induced by transcutaneous immunization and isotype switching to predominantly IgG is generally achieved with T-cell help and activation of both Th1 and Th2 pathways is suggested by the production of IgG1 and IgG2a. Alternatively, a large antibody response may be induced by a thymus-independent antigen type 1 (TI-1) which directly activates the B cell.

The spectrum of more commonly known skin immune responses is represented by contact dermatitis and atopy. Contact dermatitis, a pathogenic manifestation of LC activation, is directed by Langerhans cells which phagocytose antigen, migrate to lymph nodes, present antigen, and sensitize T cells for the intense destructive cellular response that occurs at the affected skin site. Atopic dermatitis may utilize the Langerhans cell in a similar fashion, but is identified with Th2 cells and is generally associated with high levels of IgE antibody.

Transcutaneous immunization may be induced via the ganglioside GM1 binding activity of CT, LT or subunits such as CTB. Ganglioside GM1 is a ubiquitous cell membrane glycolipid found in all mammalian cells. When the pentameric CT B subunit binds to the cell surface a hydrophilic pore is formed which allows the A subunit to pentrate across the lipid bilayer.

Transcutaneous immunization by CT or CTB may require ganglioside GM1 binding activity. When mice were transcutaneously immunized with CT or CTA and CTB, only CT and CTB resulted in an immune response. CTA contains the ADP-ribosylating exotoxin activity, but only CT and CTB containing the binding activity were able to induce an immune response, indicating that the B subunit was necessary and sufficient to immunize through the skin. As a result, it can be concluded that Langerhans cells may be activated by CTB binding to its cell surface.

Optionally, an activator of Langerhans cells may be used as an adjuvant. Examples of such activators include: inducers of heat shock protein; contact sensitizers (e.g., trinitrochlorobenzene, dinitrofluorobenzene, nitrogen mustard, pentadecylcatechol); toxins (e.g., Shiga toxin, Staph enterotoxin B); lipopolysaccharides, lipid A, or derivatives thereof; bacterial DNA (Stacey et al., "Macrophages Ingest and are Activated by Bacterial DNA," *J. Immunol.* 157:2116–22 (1996), which is hereby incorporated by reference in its entirety); cytokines (e.g., tumor necrosis factor, interleukin-1β, -10, -12); and chemokines (e.g., defensins 1 or 2, RANTES, MIP-1α, MIP-2, interleukin-8).

If an immunizing antigen has sufficient Langerhans cell activating capabilities, then a separate adjuvant may not be required, as in the case of CT which both antigen and adjuvant. It is envisioned that whole cell preparations, live viruses, attenuated viruses, DNA plasmids, and bacterial DNA could be sufficient to immunize transcutaneously. It may be possible to use low concentrations of contact sensitizers or other activators of Langerhans cells to induce an immune response without inducing skin lesions.

Immunization may be achieved using epicutaneous application of a simple solution of antigen and adjuvant impregnated in gauze under an occlusive patch, or by using other patch technologies, creams, immersion, ointments and sprays are other possible methods of application.

The transcutaneous immunization system may be applied; directly to the skin and allowed to air dry; rubbed into the skin or scalp; held in place with a dressing, patch, or absorbent material; otherwise held by a device such as a stocking, slipper, glove, or shirt; or sprayed onto the skin to maximize contact with the skin.

The formulation may be applied in an absorbent dressing or gauze. The formulation may be covered with an occlusive dressing such as AQUAPHOR (an emulsion of petrolatum, mineral oil, mineral wax, wool wax, panthenol, bisabol, and glycerin from Beiersdorf, Inc.), plastic film, COMFEEL (Coloplast) or vaseline; or a non-occlusive dressing such as, for example, DUODERM (3M) or OPSITE (Smith & Nephew). An occlusive dressing completely excludes the passage of water.

The formulation may be applied to single or multiple sites, to single or multiple limbs, or to large surface areas of the skin by complete immersion. The formulation may be applied directly to the skin.

EXAMPLES

Example 1

Animals

Female BALB/c mice were used at ages ranging from 8 to 12 weeks.

All animals were housed and used in accordance with institutional guidelines.

Example 2

Antigens

Methods used for the production and purification of baculovirus-expressed HPV-18 L1 VLPs has been described previously (Rose et al., "Serological Differentiation of Human Papillomavirus Types 11, 16 and 18 using Recombinant Virus-like Particles," *Journal of General Virology* 75:2445–2449 (1994); Rose et al., "Expression of Human Papillomavirus Type 11 L1 Protein in Insect Cells: in vivo and in vitro Assembly of Viruslike Particles," *Journal of Virology* 67:1936–1944 (1993), which are hereby incorporated by reference in their entirety).

Example 3

Adjuvants

E. coli LT R192G was produced as previously described (Dickinson et al., "Dissociation of Escherichia coli Heat-Labile Enterotoxin Adjuvanticity from ADP-Ribosyltransferase Activity," Infection & Immunity 63:1617–1623 (1995), which is hereby incorporated by reference in its entirety) and reconstituted in sterile PBS (1 mg/ml) prior to use.

Example 4

Immunizations

Mice were shaved 24 hours prior to transdermal administration of 100 ul of PBS containing 50 µg of HPV-18 VLPs with or without 50 µg of E. coli LT R192G. Control mice were immunized orally with 5 µg of VLPs plus 5 µg of LT R192G.

Example 5

Enzyme-linked Immunosorbent Assay (ELISA)

Pre- and post-immune sera were obtained by retrobulbar collection.

VLP antibody levels were measured in an ELISA, as previously-described (Rose et al., "Oral Vaccination of Mice with Human Papillomavirus Virus-like Particles Induces Systemic Virus-Neutralizing Antibodies" Vaccine 17:2129–2135 (1999), which is hereby incorporated by reference in its entirety). Briefly, Nunc MaxiSorp™ (Nalgene, Denmark) 96-well microtiter plates were coated with 0.1 µg of antigen in PBS per well, incubated at 4° C. overnight, blocked with 2% BSA (Diluent/Blocking solution, Kirkegaard and Perry (K&P) Laboratories, Gaithersburg, Md.), and washed four times with 0.05% Tween 20 in PBS. Test sera were diluted 1:50 in BSA diluent/blocking solution (K&P Laboratories) and incubated for 90 min at room temperature to permit antibody binding. Plates were washed as before and reacted for 90 minutes at room temperature with alkaline phosphatase-conjugated goat anti-mouse IgG (Southern Biotechnology Associates, Inc., Birmingham, Ala.) diluted 1:5,000 in BSA diluent/blocking solution. The reaction was developed with 100 µl per well of substrate (p-nitrophenyl phosphate, Sigma Chemicals, Inc., St. Louis, Mo.) for 1 hour. Absorbance measurements were made at 405 nm using an automated plate reader.

Example 6

Evaluation of VLP Polyclonal Antibody Specificities

VLP post-immune sera were tested in an ELISA against native and denatured VLPs of HPV-18, and against native VLPs of HPV-16, as previously described (Gerber et al., "Human Papillomavirus Virus-like Particles are Efficient Oral Immunogens When Co-administered with Escherichia coli Heat-labile Enterotoxin Mutant R192G or CpG DNA," Journal of Virology 75:4752–4760 (2001), which is hereby incorporated by reference in its entirety).

Example 7

TCI-induced anti-VLP Serum IgG Response

To evaluate VLP transdermal immunogenicity, mice (female Swiss-Webster; N=6/group) were immunized transdermally with HPV-18 VLPs at two dose levels (5 or 50 µg), in combination with LT R192G at either of two dose levels (5 or 50 µg). Mice were boosted at 2 and 4 weeks after primary immunizations, and sera were collected two weeks after the second boost and evaluated in an ELISA for anti-VLP antibodies. Mice immunized transdermally with 50 µg of VLPs in combination with 50 µg of LT R192G (i.e., the highest dose levels of each) demonstrated serum IgG titers that were elevated over those induced by VLPs without adjuvant (FIG. 1).

Example 8

TCI-induced VLP Polyclonal Antibody Specificities

Figure 2:
FIG. 2 shows conformational dependence and HPV genotype-specificity of serum IgG responses after transcutaneous immunization with HPV-18 VLPs. High-responder post-immune sera (see FIG. 1) were evaluated in an ELISA for VLP antibody specificities. Sera were tested against native and denatured HPV-18 VLPs, and native HPV-16 VLPs (Rose et al., "Serological Differentiation of Human Papillomavirus Types 11, 16 and 18 Using Recombinant Virus-like Particles," *Journal of General Virology* 75:2445–2449 (1994); Rose et al., "Human Papillomavirus Type 11 Recombinant L1 Capsomeres Induce Virus-Neutralizing Antibodies," *Journal of Virology* 72(7):6151–6154 (1998); Rose et al., "Oral Vaccination of Mice with Human Papillomavirus Virus-like Particles Induces Systemic Virus-Neutralizing Antibodies," *Vaccine* 17:2129–2135 (1999), which are hereby incorporated by reference in their entirety).

VLP-induced virus-neutralizing polyclonal antibody specificities characteristically exhibit the properties of conformational dependence and virus genotype specificity (Giroglou et al., "Immunological Analyses of Human Papillomavirus Capsids," Vaccine 19:1783–1793 (2001), which is hereby incorporated by reference in its entirety). To examine whether potentially protective serum antibody specificities (i.e., conformationally dependent and HPV genotype-specific) antibody specificities were induced by TCI, post-immune sera were evaluated in an ELISA against native HPV-18 VLPs (ie., the same antigen used for immunization), denatured HPV-18 VLPs, and against native HPV-16 VLPs (a heterologous HPV genotype). Results indicated that co-administration of native HPV-18 VLPs with LT R192G by TCI induced antibody specificities with properties that are characteristically associated with HPV virion-neutralizing antibody specificities. (FIG. 2).

HPV VLP transcutaneous immunogenicity was assessed in mice. VLPs of oncogenic anogenital HPV type 18 were found to be immunogenic when administered by this route, and to induce conformationally dependent and genotype-specific IgG serum antibody responses. Although virion neutralization has not been assessed directly, the work of several groups has consistently indicated a strong correlation between VLP ELISA titers and virion/pseudovirion neutralization titers in vitro (Balmelli et al., "Nasal Immunization of Mice with Human Papillomavirus Type 16 Virus-like Particles Elicits Neutralizing Antibodies in Mucosal Secretions," Journal of Virology 72:8220–8229 (1998); Roden et al., "In vitro Generation and Type-Specific Neutralization of a Human Papillomavirus Type 16 Virion Pseudotype," Journal of Virology 70:5875–5883 (1996); Rose et al., "Oral Vaccination of Mice with Human Papillomavirus Virus-like Particles Induces Systemic Virus-Neutralizing Antibodies" Vaccine 17:2129–2135 (1999); Rose et al., "Human Papillomavirus Type 11 Recombinant L1 Capsomeres Induce Virus-Neutralizing Antibodies," Journal of Virology 72(7): 6151–6154 (1998); Unckell et al., "Generation and Neutralization of Pseudovirions of Human Papillomavirus Type 33," Journal of Virology 71:2934–2939 (1997); White et al., "In vitro Infection and Type-Restricted Antibody-Mediated Neutralization of Authentic Human Papillomavirus Type 16," Journal of Virology 72:959–964 (1998), which are hereby incorporated by reference in their entirety), and in vivo (Bryan et al., "Human Papillomavirus Type 11 Neutralization in the Athymic Mouse Xenograft System: Correlation With Virus-like Particle IgG Concentration," J Med Virol. 53:185–8 (1997); Christensen et al., "Human Papillomavirus Types 6 and 11 have Antigenically Distinct Strongly Immunogenic Conformationally Dependent Neutralizing Epitopes," Virology 205:329–335 (1994); Rose et al., "Human Papillomavirus (HPV) Type 11 Recombinant Virus-like Particles Induce the Formation of Neutralizing Antibodies and Detect HPV-specific Antibodies in Human Sera," *Journal of General Virology* 75:2075–2079 (1994), which are hereby incorporated by reference in their entirety). Consequently, the VLP ELISA is regarded as an excellent surrogate assay for the detection of virus-neutralizing activity (Schiller, J. T., "Papillomavirus-like Particle Vaccines for Cervical Cancer," *Molecular Medicine Today* 5:209–215 (1999), which is hereby incorporated by reference in its entirety). Thus, the results indicate that VLPs are immunogenic when co-administered with adjuvant by a transcutaneous route thus suggesting that VLP TC1 may be an effective or useful strategy for controlling anogenital HPV disease.

Preclinical studies of VLPs using alternate immunization routes have been limited (Balmelli et al., "Nasal Immunization of Mice with Human Papillomavirus Type 16 Virus-like Particles Elicits Neutralizing Antibodies in Mucosal Secretions," *Journal of Virology* 72:8220–8229 (1998); Dupuy et al., "Nasal Immunization of Mice with Human Papillomavirus Type 16 (HPV-16) Virus-like Particles or with the HPV-16 L1 Gene Elicits Specific Cytotoxic T Lymphocytes in Vaginal Draining Lymph Nodes," *Journal of Virology* 73:9063–9071 (1999); Liu et al., "Mucosal Immunisation with Papillomavirus Virus-like Particles Elicits Systemic and Mucosal Immunity in Mice," *Virology* 252:39–45 (1998); Nardelli-Haefliger et al., "Mucosal But not Parenteral Immunization with Purified Human Papillomavirus Type 16 Virus-like Particles Induces Neutralizing Titers of Antibodies Throughout the Estrous Cycle of Mice," *Journal of Virology* 73:9609–9613 (1999); Nardelli-Haefliger et al., "Human Papillomavirus Type 16 Virus-like Particles Expressed in Attenuated *Salmonella Typhinurium* Elicit Mucosal and Systemic Neutralizing Antibodies in Mice," *Infection & Immunity* 65:3328–3336 (1997); Rose et al., "Oral Vaccination of Mice with Human Papillomavirus Virus-like Particles Induces Systemic Virus-Neutraliing Antibodies" *Vaccine* 17:2129–2135 (1999), which are hereby incorporated by reference in their entirety), and an optimal alternate method of immunization has not yet been defined. Other groups investigating alternate immunization strategies have reported that anti-VLP serum IgG and vaginal IgA antibody responses were induced after intranasal immunization of mice with HPV-16 VLPs co-formulated with CT (Balmelli et al., "Nasal Immunization of Mice with Human Papillomavirus Type 16 Virus-like Particles Elicits Neutralizing Antibodies in Mucosal Secretions," *Journal of Virology* 72:8220–8229 (1998); Dupuy et at, "Nasal Immunization of Mice with Human Papillomavirus Type 16 (HPV-16) Virus-like Particles or With the HPV-16 L1 Gene Elicits Specific Cytotoxic T Lymphocytes in Vaginal Draining Lymph Nodes," *Journal of Virology* 73:9063–9071 (1999), which are hereby incorporated by reference in their entirety). Balmelli et al (Balmelli et al., "Nasal Immunization of Mice with Human Papillomavirus Type 16 Virus-like Particles Elicits Neutralizing Antibodies in Mucosal Secretions," *Journal of Virology* 72:8220–8229 (1998), which is hereby incorporated by reference in its entirety) found that VLPs were immunogenic when administered intranasally, but poorly immunogenic when administered orally with or without CT (Balmelli et al., "Nasal Immunization of Mice with Human Papillomavirus Type 16 Virus-like Particles Elicits Neutralizing Antibodies in Mucosal Secretions," *Journal of Virology* 72:8220–8229 (1998), which is hereby incorporated by reference in its entirety). Similarly, Dupuy et al. (Dupuy et al., "Nasal Immunization of Mice with Human Papillomavirus Type 16 (HPV-16) Virus-like Particles or With the HPV-16 L1 Gene Elicits Specific Cytotoxic T Lymphocytes in Vaginal Draining Lymph Nodes," *Journal of Virology* 73:9063–9071 (1999), which is hereby incorporated by reference in its entirety) reported anti-HPV-16 VLP serum IgG titers greater than $10^4$, and vaginal IgA titers greater than $10^2$, after intranasal administration of VLPs with CT, whereas VLPs administered intranasally without CT were only poorly immunogenic (Dupuy et al., "Nasal Immunization of Mice with Human Papillomavirus Type 16 (HPV-16) Virus-like Particles or With the HPV-16 L1 Gene Elicits Specific Cytotoxic T Lymphocytes in Vaginal Draining Lymph Nodes," *Journal of Virology* 73:9063–9071 (1999), which is hereby incorporated by reference in its entirety). Previous results (Gerber et al., "Human Papillomavirus Virus-like Particles are Efficient Oral Immunogens When Co-Administered with *Escherichia coli* Heat-Labile Enterotoxin Mutant R192G or CpG DNA," *Journal of Virology* 75:4752–4760 (2001); Rose et al., "Oral Vaccination of Mice with Human Papillomavirus Virus-like Particles Induces Systemic Virus-Neutralizing Antibodies" *Vaccine* 17:2129–2135 (1999), which are hereby incorporated by reference in their entirety) indicate that VLPs are efficient oral immunogens when co-administered with *E. coli* LT R192G. The present results indicate that similar effects can be achieved when HPV VLPs are administered by a transcutaneous route of delivery.

Vaccines represent the most efficient and cost-effective means of preventing disease; however, the full potential of vaccination to improve public health is not yet realized (Katz, S. L., "Future Vaccines and a Global Perspective," *Lancet* 350:1767–1770 (1997), which is hereby incorporated by reference in its entirety). Vaccines that can be delivered by a transcutaneous route offer practical and financial advantages over parenterally administered vaccines. From a practical standpoint, transcutaneous vaccines are easier to administer and less invasive than parenteral vaccines and, thus, are more likely to facilitate mass vaccination programs in underdeveloped regions. The development of needle-free vaccines has a high priority, in part due to the recognition that blood-born diseases are often transmitted through the reuse of needles (Aylward et al., "Reducing the Risk of Unsafe Injections in Immunization Programmes: Financial and Operational Implications of Various Injection Technologies," *Bulletin of the World Health Organization* 73:531–540 (1995); Reeler, A. V., "Anthropological Perspectives on Injections: a Review," *Bulletin of the World Health Organization* 78:135–143 (2000), which are hereby incorporated by reference in their entirety). The relative simplicity of transcutaneous immunization could very well facilitate vaccine distribution in developing regions, which bear the brunt of genital HPV disease (Bosch et al., "Prevalence of Human Papillomavirus in Cervical Cancer: a Worldwide Perspective. International Biological Study on Cervical Cancer (IBSCC) Study Group," *Journal of the National Cancer Institute* 87:796–802 (1995), which is hereby incorporated by reference in its entirety).

Example 9

Serum IgG Responses After Transcutaneous Immunization with HPV VLPs

Figure 3:
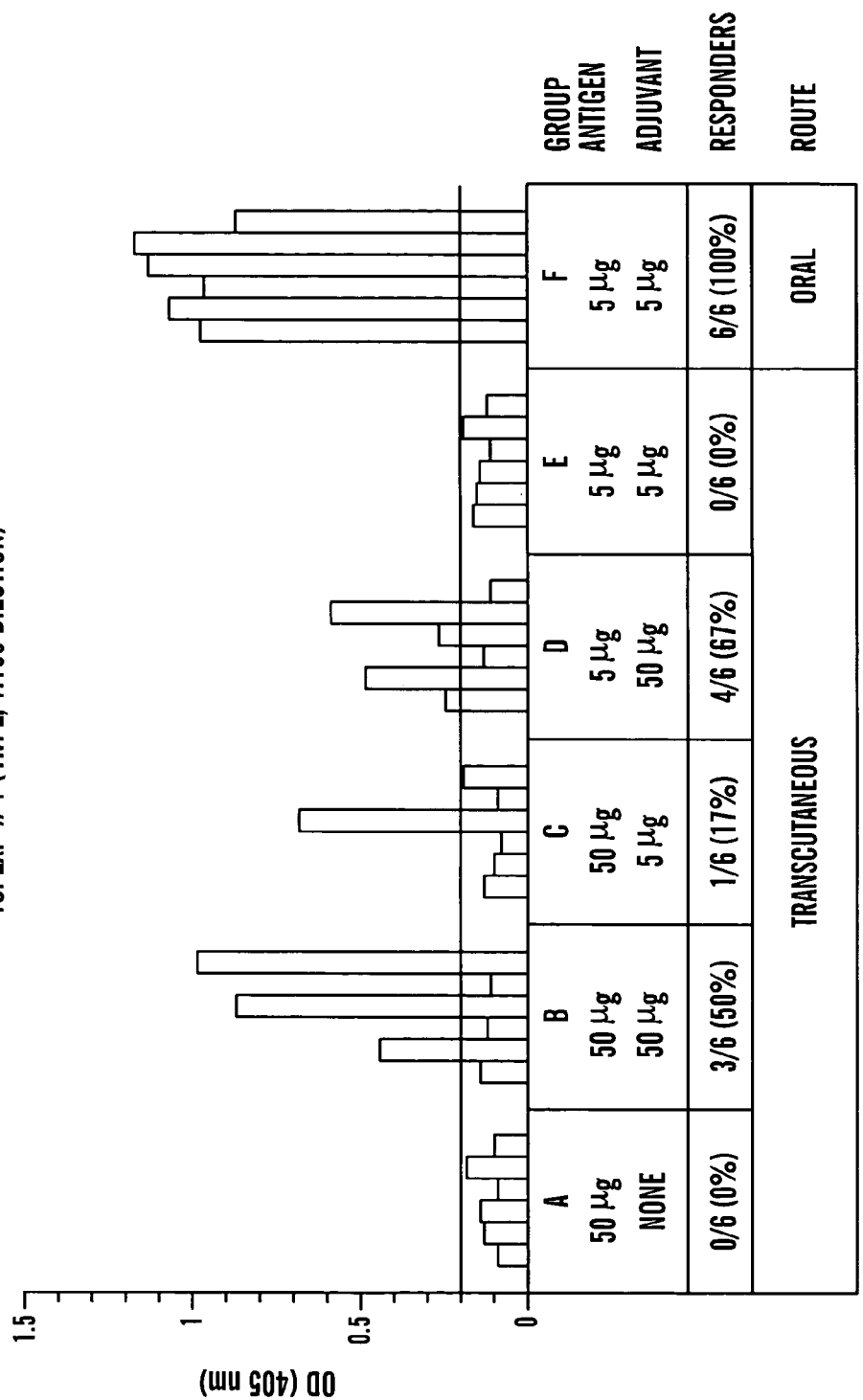
FIG. 3 describes VLP serum IgG responses after transcutaneous immunization. Female BALB/c mice (6/group) were immunized as indicated; sera were collected and evaluated by ELISA against HPV-18 VLPs as previously described in Rose et al., "Serological Differentiation of Human Papillomavirus Types 11, 16 and 18 Using Recombinant Virus-like Particles," *Journal of General Virology* 75:2445–2449 (1994), which is hereby incorporated by reference in its entirety.

Female BALB/c mice (6/group) were immunized as indicated, sera were collected and evaluated by ELISA against HPV-18 VLPs as previously described (Rose et al., "Human Papillomavirus (HPV) Type 11 Recombinant Virus-Like Particles Induce the Formation of Neutralizing Antibodies and Detect HPV-Specific Antibodies in Human Sera," *Journal of General Virology* 75:2075–2079 (1994), which is hereby incorporated by reference in its entirety). See FIG. 3.

Example 10

Figure 4:
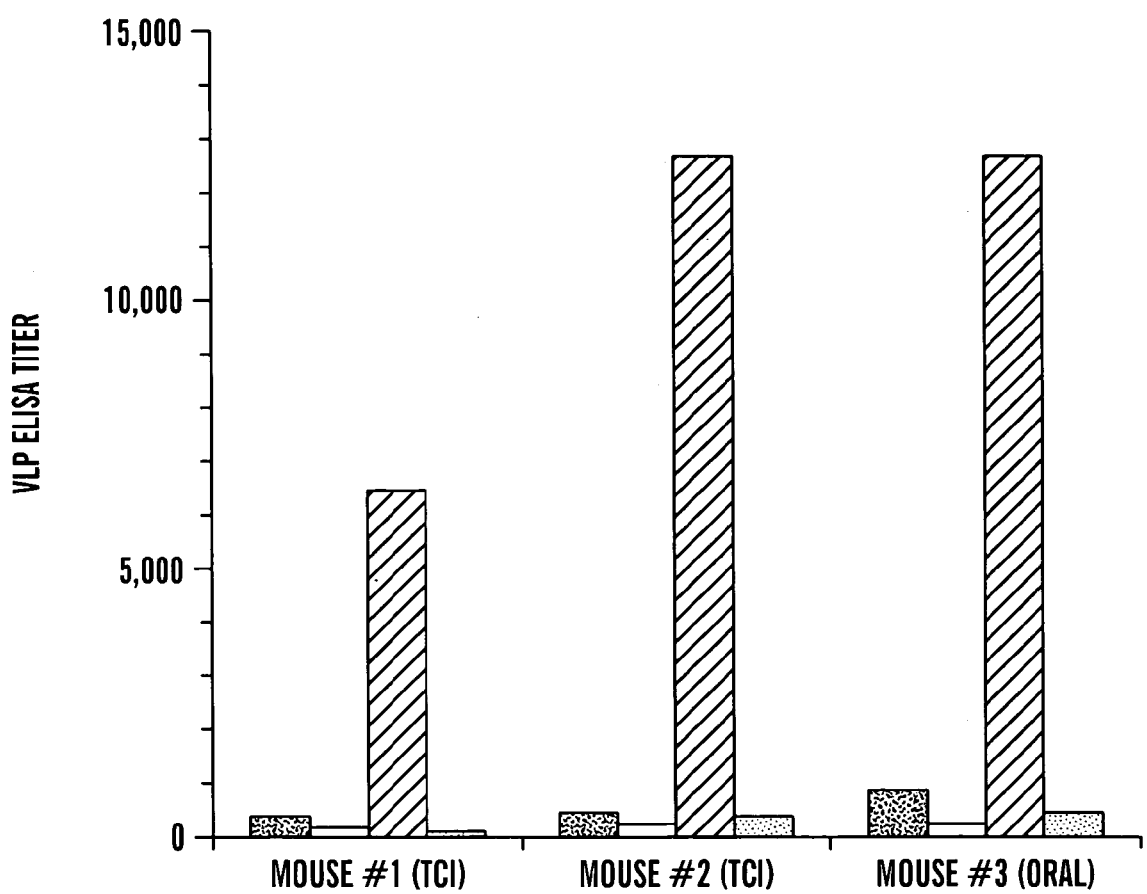
FIG. 4 shows VLP antibody specificities after transcutaneous immunization. HPV-18 VLPs were administered as described (see above description of FIG. 3) and post-immune sera were evaluated in a VLP ELISA against native and denatured VLPs of HPV types 16 and 18. Native HPV-16 VLPs (black); denatured HPV-16 VLPs (white); native HPV-18 VLPs (striped); denatured HPV-18 VLPs (gray). Mouse #1 and Mouse #2 sera are from Group B; control Mouse #3 serum is from Group F (see above description of FIG. 1). These results indicate that recombinant papillomavirus VLPs are immunogenic when administered by a transcutaneous route, and that the antibody specificities induced by this method are conformationally dependent and virus genotype-specific. These properties have been correlated with antibody-mediated neutralization of infectious papillomavirus virions in vitro and in vivo (Rose et al., "Serological Differentiation of Human Papillomavirus Types 11, 16 and 18 Using Recombinant Virus-like Particles," *Journal of General Virology* 75:2445–2449 (1994); Suzich et al., "Systemic Immunization With Papillomavirus L1 Protein Completely Prevents the Development of Viral Mucosal Papillomas," *Proceedings of the National Academy of Sciences of the United States of America* 92:11553–11557 (1995); and White et al., "In vitro Infection and Type-Restricted Antibody-Mediated Neutralization of Authentic Human Papillomavirus Type 16," *Journal of Virology* 72:959–964 (1998), which are hereby incorporated by reference in their entirety).

Antigenic Specificities of Serum IgG Responses After Transcutaneous Immunization Administration of HPV VLPs HPV-18 VLPs were administered as described in Example 9 and post-immune sera were evaluated in a VLP ELISA against native and denatured VLPs of HPV types 16 and 18. FIG. 4 shows native HPV-16 VLPs (black); denatured HPV-16 VLPs (white); native HPV-18 VLPs (striped); denatured HPV-18 VLPs (gray). Mouse #1 and Mouse #2 sera are from Group B; control Mouse #3 serum is from Group F (see description of FIG. 3 supra).

These results indicate that recombinant papillomavirus VLPs are immunogenic when administered by a transcutaneous route, and that the antibody specificities induced by this method are conformationally dependent and virus genotype-specific. These properties have been correlated with antibody-mediated neutralization of infectious papillomavirus virions in vitro and in vivo (Rose et al., "Human Papillomavirus (HPV) Type 11 Recombinant Virus-Like Particles Induce the Formation of Neutralizing Antibodies and Detect HPV-Specific Antibodies in Hman Sera," *Journal of General Virology* 75:2075–2079 (1994); Suzich et al., "Systemic Immunization With Papillomavirus L1 Protein Completely Prevents the Development of Viral Mucosal Papillomas," *Proceedings of the National Academy of Sciences of the United States of America* 92:11553–11557 (1995); and White et al., "In Vitro Infection and Type-Restricted Antibody-Mediated Neutralization of Authentic Human Papillomavirus Type 16," *Journal of Virology* 72:959–964 (1998), which are hereby incorporated by reference in their entirety).

Example 11

Durability of Transdermal Priming and Parenteral Booster Response

Figure 5:
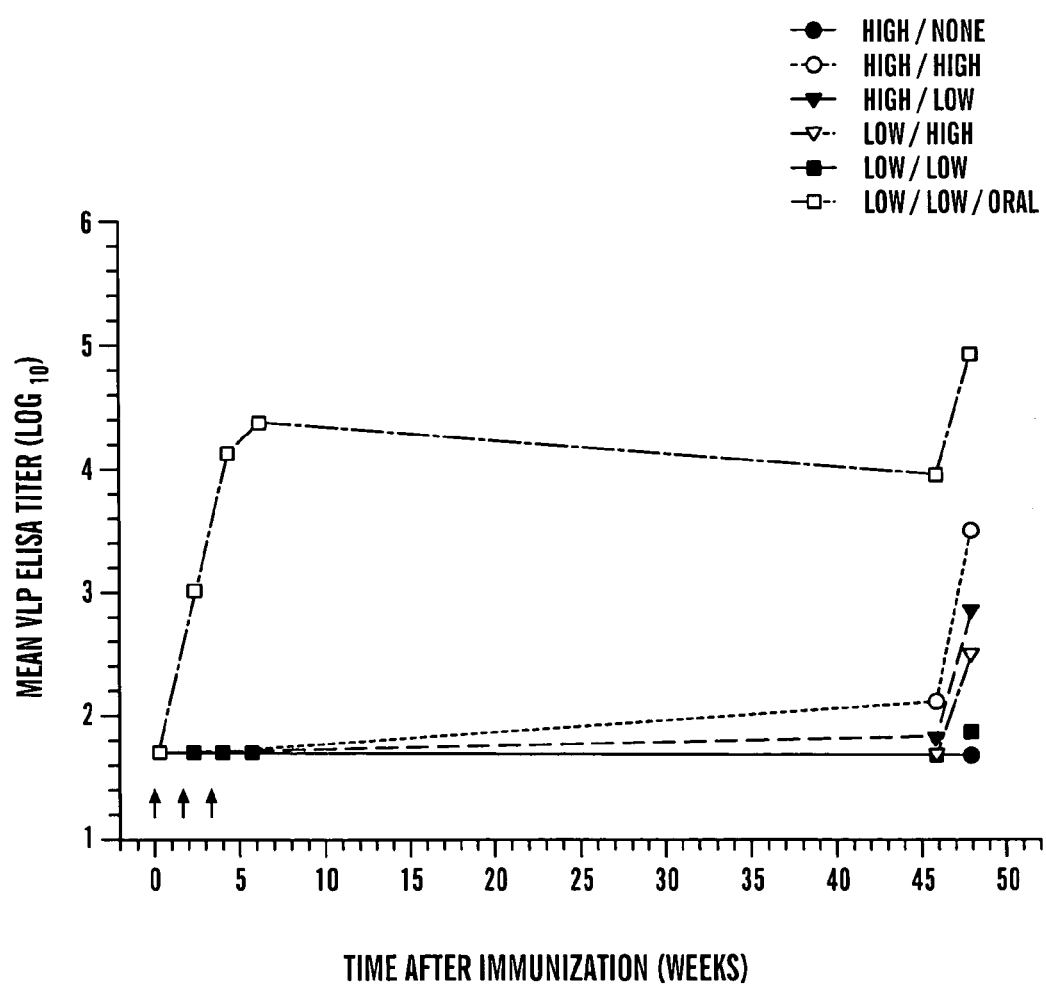
FIG. 5 shows the durability of transdermal priming and parenteral booster response. Female BALB/c mice (N=6/group) were immunized and boosted (arrows) by transdermal or oral inoculation below. At 46 weeks post-immunization, all mice were boosted (0.5 µg VLPs; no adjuvant) by parenteral (intramuscular) injection.

Female BALB/c mice (N=6/group) were immunized and boosted (arrows) by transdermal or oral inoculation (see below). At 46 weeks post-immunization, all mice were boosted (0.5 µg VLPs; no adjuvant) by parenteral (intramuscular) injection. See FIG. 5.

Primary and initial booster immunizations were administered as follows in Table 1:

TABLE 1

| Group | Symbol | Immunization Route | Antigen | Adjuvant |
|---|---|---|---|---|
| A | Filled circles | Transdermal | 50 µg VLP | None |
| B | Open circles | Transdermal | 50 µg VLP | 50 µg LT(R192G) |
| C | Filled diamonds | Transdermal | 50 µg VLP | 5 µg LT(R192G) |
| D | Open diamonds | Transdermal | 5 µg VLP | 50 µg LT(R192G) |
| E | Filled squares | Transdermal | 5 µg VLP | 5 µg LT(R192G) |
| F | Open squares | Oral | 5 µg VLP | 5 µg LT(R192G) |

These results indicate that VLP transdermal immunization initiates an immune response that is dose-dependent with regard to antigen and adjuvant, and that such responses are highly durable as indicated by strong responses to boosting at 1 year after primary immunizations. In addition, the rise in VLP-specific antibody titers in mice immunized transdermally stands in contrast to the decline in antibody titers seen in mice immunized by oral gavage, indicating sequestration and slow-release of transdermally-administered immunogen over time.

The above results indicate that a robust potentially protective immune response can be generated by topical co-administration of a large complex antigen with adjuvant. Human papillomavirus (HPV) virus-like particles (VLPs; molecular mass ~19,800,000 Daltons) exceed the mass of the largest antigens administered previously by a transdermal route. This result was unexpected as it has been stated in the literature that large size would likely preclude or inhibit entry via intact epidermis. For example, previously Glenn et al., *Nature*, 391:851 (1998) reported that diptheria toxin (MW~60 kD) and tetanus toxin (MW~150 kD) were immunogenic when co-administered transdermally with cholera toxin. However, tetanus toxin was reported to be approximately 10-fold less immunogenic than was diptheria toxin, thus suggesting a possible size effect in the generation of responses to transdermal immunization. As demonstrated above, the VLPs of the present invention are immunogenic when administered transdermally, and that VLP transdermal administration can activate the immune system for response to boosting by other routes of immunization (e.g., by parenteral injection or oral administration) up to one year following primary immunizations. Moreover, applicant's previously reported results indicate that VLP-specific antibody titers decline slowly during the period following primary and booster inoculations when VLPs are administered by either oral or parenteral routes of immunization By contrast, the above results indicate that VLP-specific antibody titers rise rather than diminish during the period following transdermal administration of VLPs. These observations support the conclusion that, unlike parenteral or oral routes of immunization, VLP transdermal administration promotes sequestration and slow release of VLP immunogens over time, which mediates long-term low-level stimulation of anti-VLP immune responses.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of inducing an immune response in a mammal against papillomavirus comprising:
   administering papillomavirus virus-like particles transcutaneously to a mammal under conditions effective to induce an immune response to the papillomavirus.

2. The method according to claim 1 further comprising:
   administering one or more vaccine booster inoculations of papillomavirus virus-like particles to the mammal.

3. The method according to claim 2, wherein said booster inoculation is administered parenterally, transdermally, or orally.

4. The method according to claim 3, wherein the booster is orally administered.

5. The method according to claim 3, wherein the booster is parenterally administered.

6. The method according to claim 3, wherein the booster is transdermally administered.

7. The method according to claim 1, wherein the immune response is an immune response which will protect the mammal from infection by papillomavirus.

8. The method according to claim 1, wherein the papillomavirus is a human papillomavirus.

9. The method according to claim 8, wherein the human papillomavirus is Human Papillomavirus Type 6.

10. The method according to claim 8, wherein the human papillomavirus is Human Papillomavirus Type 11.

11. The method according to claim 8, wherein the human papillomavirus is Human Papillomavirus Type 16.

12. The method according to claim 8, wherein the human papillomavirus is Human Papillomavirus Type 18.

13. The method according to claim 8, wherein the papillomavirus virus-like particles are administered with a pharmaceutically acceptable carrier.

\* \* \* \* \*

UNITED STATES PATENT AND TRADEMARK OFFICE
CERTIFICATE OF CORRECTION

| | | |
|---|---|---|
| PATENT NO. | : 7,247,433 B2 | Page 1 of 1 |
| APPLICATION NO. | : 10/486564 | |
| DATED | : July 24, 2007 | |
| INVENTOR(S) | : Robert C. Rose | |

It is certified that error appears in the above-identified patent and that said Letters Patent is hereby corrected as shown below:

Col. 1 at lines 9-12, delete "The United States Government may have certain rights in this invention pursuant to a Public Health Service award from the National Institutes of Health (Grant No. 1R01 CA 84105-01)" and insert --This invention was made with government support under grant CA084105 awarded by the National Institutes of Health. The government has certain rights in the invention-- in its place.

Signed and Sealed this

Twentieth Day of May, 2008

JON W. DUDAS
*Director of the United States Patent and Trademark Office*